United States Patent [19]
Stevens et al.

[11] Patent Number: 4,650,299
[45] Date of Patent: Mar. 17, 1987

[54] VISUAL COMMUNICATION SYSTEM

[75] Inventors: Edward P. Stevens, Menomonie; Robert Godbarsen, Oconomowoc, both of Wis.

[73] Assignee: General Electric Company, Milwaukee, Wis.

[21] Appl. No.: 655,660

[22] Filed: Sep. 28, 1984

[51] Int. Cl.⁴ .............................................. G02B 5/08
[52] U.S. Cl. ..................................... 350/626; 350/639
[58] Field of Search ............... 350/618, 622, 626, 632, 350/639

[56] References Cited

U.S. PATENT DOCUMENTS 3,019,689  2/1962  Paulsrud ............................. 350/618
3,804,495  4/1974  Rayow et al. ....................... 350/622
4,531,813  7/1985  Van den Berg ..................... 350/632

Primary Examiner—John K. Corbin
Assistant Examiner—Vincent J. Lemmo
Attorney, Agent, or Firm—Alexander M. Gerasimow; Douglas E. Stoner

[57] ABSTRACT

A visual communication system is disclosed which presents a patient confined in a diagnostic tunnel with an upright image of an observer positioned outside the tunnel regardless of the patient's axial position in the tunnel and which allows the observer to remain in visual contact with the patient.

7 Claims, 3 Drawing Figures

VISUAL COMMUNICATION SYSTEM

The present invention relates in general to visual communication systems, and in particular to apparatus which allows a patient in a confined space to maintain visual contact with an observer positioned outside.

BACKGROUND OF THE INVENTION

Certain types of medical examinations require that the patient be placed into an enclosed space, e.g., a tunnel, in order that specialized equipment, such as magnetic resonance apparatus, may be used to perform tests on the patient. For example, magnetic resonance head imaging requires placing a supine patient's head into a head coil and positioning the patient such that his head is located at the center of the magnet tunnel. When the patient has been partially, or fully inserted into the magnet tunnel, it is difficult or impossible for him to view any activity outside the tunnel, and it is likewise difficult or impossible for the operator to see the patient's eyes. The ability of a patient to view activity outside the tunnel helps to reduce feelings of anxiety and claustrophobia. Further, it is desirable for the operator of the equipment to sight into the tunnel and to maintain eye contact with the patient during the examination. This is important for detecting changes in the patient's physical condition; to enlist the patient's aid while the examination is in progress; and to reassure the patient that he is not being left alone.

With existing diagnostic equipment, such as magnetic resonance apparatus, or the like, it has proven difficult or impossible to maintain visual contact between a patient confined in the tunnel and an observer stationed outside. As a consequence, visual observation of the patient is precluded while the patient is in the tunnel, patient cooperation is minimized, and patient apprehension may be increased.

OBJECTS OF THE INVENTION

It is a principal object of the present invention to provide a new and improved system for maintaining visual contact between a patient in an enclosed space and an observer positioned outside.

It is another object of this invention to provide a new and improved communication system by which the operator of diagnostic apparatus can visually monitor a patient who is partially or completely confined inside such apparatus.

It is a further object of the present invention to provide a new and improved visual communication system which can assist an operator in enlisting cooperation from a patient while testing is in progress.

It is an additional object of the present invention to provide a new and improved visual communication system which can assist in allaying a patient's apprehension while he is confined inside diagnostic apparatus.

It is yet another object of the present invention to provide an upright visual image to a patient placed in a supine position inside the tunnel of magnetic resonance apparatus of an observer or of activity outside the tunnel.

SUMMARY OF THE INVENTION

The present invention is directed to a visual communication system wherein a patient positioned on a supporting platform in a tunnel is provided with a view of an observer, or of other activity, outside the tunnel and wherein the observer can view the patient's eyes. The viewing system in accordance with the invention includes at least one reflective surface, and it provides the patient with an upright view of the observer at any axial position of the patient inside the tunnel.

These and other objects of the present invention, together with the features and advantages thereof, will become apparent from the following detailed specification, when read in conjunction with the accompanying drawings in which applicable reference numerals have been carried forward.

DETAILED DESCRIPTION OF THE INVENTION

Figure 1:
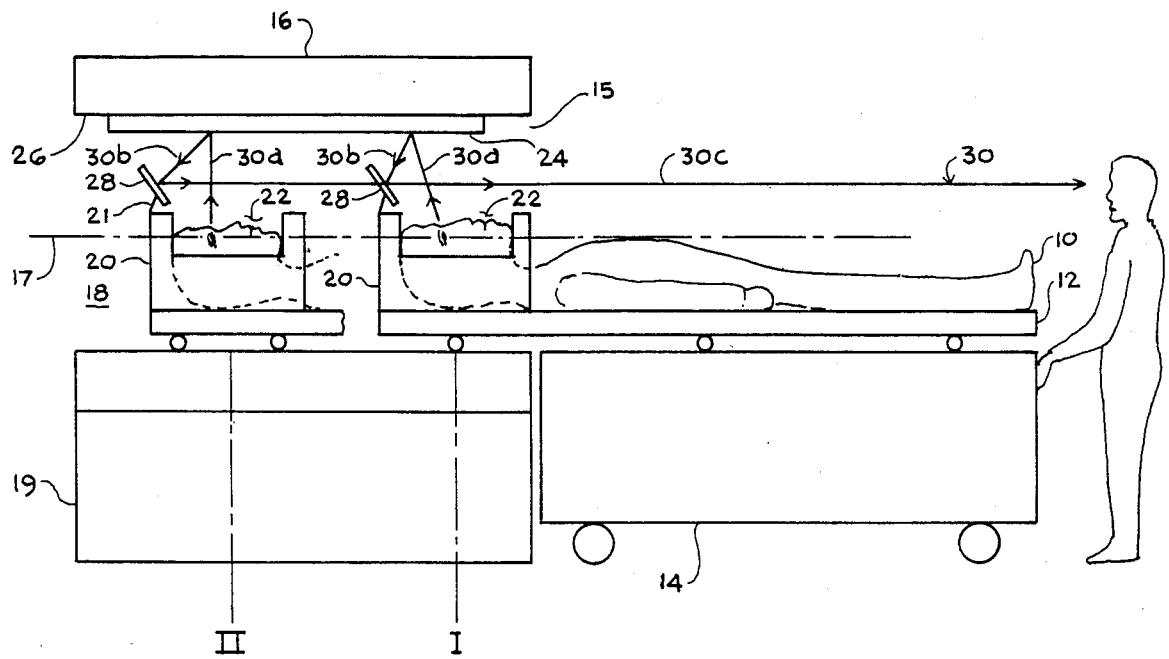
FIG. 1 illustrates a preferred embodiment of the present invention.

With reference now to the drawings, FIG. 1 illustrates a preferred embodiment of the present invention. A patient 10 is supported on a patient-bearing platform 12, which is movably supported on a patient table 14. In FIG. 1, the patient is shown entering a substantially linear diagnostic tunnel 18, head first through an opening 15 at the forward end of the tunnel, while supported on the platform 12. The tunnel 18 is part of a magnetic resonance diagnostic apparatus, which includes a magnet 16 mounted in a base 19. The magnet 16 completely surrounds a portion of the patient and the platform. The tunnel 18 is formed in the center of the magnet 16, and the patient, when positioned in the tunnel, is parallel to tunnel axis 17. As shown in the drawing, a helmet structure 20 substantially surrounds the patient's head. A window 22 in the helmet structure 20 enables the patient to look straight ahead.

The apparatus illustrated in FIG. 1 further includes a viewing system comprising a pair of reflective surfaces, preferably in the form of a pair of mirrors. A first mirror 24 is affixed to an interior wall 26 of the tunnel 18 and is seen to extend substantially between the forward and rear ends of the tunnel, i.e., the full tunnel length. Mirror 24 is spaced from the patient and is parallel to axis 17. A second mirror 2 is mounted on the helmet structure 20 and is angularly adjustable to establish a visual path 30 between the patient and an observer 32 positioned outside the tunnel along axis 17. Thus, the patient is able to sight through the window 22 and through the opening 15, to the outside of the tunnel. The visual path 30 consists of a path portion 30a, extending between the patient and mirror 24; a path portion 30b, extending between mirrors 24 and 28; and a path portion 30c, which is substantially parallel to axis 17, extending between the mirror 28 and the observer 32. The mirror 28 may be mounted directly on the helmet structure 20, or on a separate bracket or visor 21 attached to the structure 20.

As shown in the particular embodiment of FIG. 1, the patient lies in a supine position on the platform 12 as he is wheeled on mobile transport table 14 toward the tunnel opening 15. Upon reaching the opening 15, the table 14 is attached to the magnet 16 in such a manner as to allow the patient-bearing platform to slide, or roll, freely from the table into the tunnel 18. Once table 14 is in position, the helmet structure 20 is placed over the patient's head and the patient is rolled head first into the tunnel on platform 12. For the sake of clarity of explanation, FIG. 1 shows two axial positions in tunnel 18 for the head of the patient: an initial position I; and a final position II. Because mirror 24 extends substantially the full length of the tunnel, the patient is able to maintain eye contact throughout his travel between positions I and II with the observer/operator, as shown in FIG. 1. In similar manner, the observer is able to maintain eye contact with the patient while the latter is moved to the final position in the tunnel. With a patient who is axially oriented so as to enter the tunnel head first, the use of at least two mirrors is mandated, in the absence of inverting lenses or other optical devices, to assure that the patient will see an upright image of the observer through tunnel opening 15.

It will, of course, be recognized that patient positioning systems other than the particular mobile transport type shown in FIG. 1 can be used within the scope of the present invention.

Figure 2:
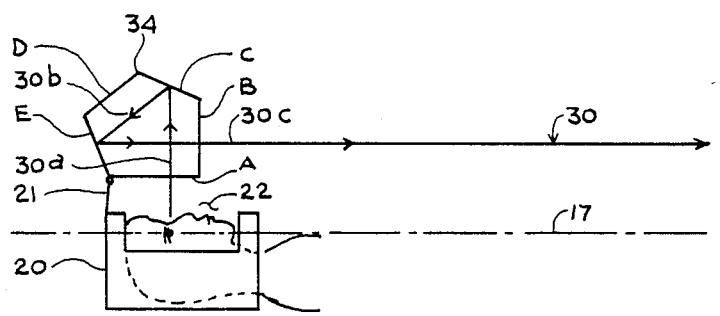
FIG. 2 illustrates another embodiment of the viewing system shown in the apparatus of FIG. 1.

FIG. 2 illustrates another embodiment of the viewing system shown in the apparatus of FIG. 1. As shown, the patient is again oriented along axis 17, with the patient's head pointing into the tunnel. A prism 34 is supported in an angularly adjustable manner on a bracket 21, which is itself affixed to helmet structure 20. The expression "prism" as used herein, is intended to designate a body of glass or the like, having a pair of multilateral, parallel, congruent bases interconnected by a plurality of lateral facets, each in the shape of a parallelogram. In the embodiment illustrated in FIG. 2, each base takes the form of a pentagon. The prism accordingly has five facets, A through E. The reflectivity of facets C and E is preferably enhanced such as by an evaporative or spattered coating process used to apply a reflective material, e.g., aluminum, to the exterior surfaces.

Prism 34 is angularly adjustable such that facet A is positioned horizontally, directly above and spaced from the supine patient's face. Facet A appears transparent to the patient. Facet C is angled relative to path portion 30a so as to reflect incident light into path portion 30b. Facet E is angled relative to path portion 30b so as to reflect incident light into path portion 30c. Path portion 30c, which is parallel to tunnel axis 17, is substantially perpendicular to facet B and is transparent to light traveling between facet E and an observer outside th tunnel. Thus, the visual path established by the viewing system shown in FIG. 2 enables the patient to see an upright image of an observer positioned along axis 17 outside the tunnel opening 15 and, conversely, it enables the observer to view the patient's eyes and the immediately adjacent facial areas.

With the viewing system shown in FIG. 2, when the patient is rolled into tunnel 18 while supported on platform 12, eye contact between patient and observer is maintained at any axial position in the tunnel. This ability stems from the fact that the prism is attached to the helmet structure which travels with the platform. Thus, the long mirror required to be mounted on the tunnel wall in the viewing system of FIG. 1 is unnecessary here and the patient receives an upright view of the observer at any position of the platform in the tunnel.

It will be recognized by those skilled in the art that the prism structure shown in FIG. 2 may be replaced with a pair of separate mirrors, i.e., a first mirror mounted in place of lateral facet C and a second mirror mounted in place of facet E, both mirrors being movable with platform 12, and at least one of them being angularly adjustable. Such a system is likewise able to establish visual path 30 between the patient and the observer and its functional and operational characteristics remain the same as where a prism is used.

Figure 3:
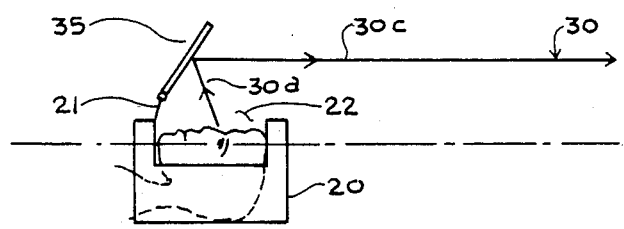
FIG. 3 illustrates a further embodiment of the viewing system for a reverse-positioned patient.

FIG. 3 illustrates a further embodiment of the present invention wherein the patient is oriented along the tunnel axis, with the patient's feet pointing into the tunnel, i.e., toward the rear tunnel end. In order to see an upright image of the observer positioned outside the tunnel opening 15 with this reverse orientation of the patient, the viewing system requires only a single mirror 35, mounted on bracket 21 which is affixed to helmet structure 20. Mirror 35 is angularly adjustable so as to maintain the desired visual path 30 between the observer and the patient. Path 30 in the present embodiment of the invention comprises only two path portions, 30a and 30c. Eye contact between patient and observer is maintained at any position of platform 12 in tunnel 18.

It should be recognized that the headholder 20 may be designed to selectively accommodate either mirror 35 for foot-entry viewing or mirror 28 for head-entry viewing, by modifying the angulation and mirror location on the headholder, and, furthermore, these mirrors may be one and the same.

The present invention is not limited to the specific embodiments illustrated and described above. For example, the components of the visual system intended to move with the patient-bearing platform need not be mounted on the helmet structure, but may be supported on a separate structure affixed directly or indirectly to the platform.

Under certain conditions, it may be necessary to position the patient on his side on the platform, rather than in a supine position on his back. For such a situation, a mirror substantially identical to mirror 24 in FIG. 1 will be mounted on the interior tunnel wall 26, parallel to axis 17 and spaced from the patient, but at a position on the wall 26 where the mirror confronts the patient when he lies on his side. Thus, with reference to FIG. 1, path portions 30a and 30b will be repositioned by 90°. Path portion 30c will remain substantially unchanged.

The invention herein is not confined to a system for visually communicating between a patient and an observer. It will be clear that the principles of the present invention may also find application in apparatus where an inanimate object is located remote from an observer in a relatively narrow, confined space and where it is desired to view such object from outside the confined space.

While specific embodiments of the invention have been described herein, it will be obvious that the invention is not so limited and that numerous variations, modifications, substitutions and equivalents, in full or in part, will now occur to those skilled in the art, all of which fall within the spirit and scope of the present invention. Accordingly, it is intended that the invention be limited only by the scope of the claims attached hereto.

The invention claimed is:

1. Apparatus for visually communicating with a patient during an examination thereof in a substantially linear diagnostic tunnel which surrounds at least a portion of said patient;

said apparatus comprising:
a platform for supporting said patient in a predetermined axial orientation in said tunnel;
means for positioning said platform in a plane parallel to the axis of said tunnel; and a viewing system mounted relative to said patient to permit a visual path to be established, at any axial position of said platform within said tunnel, between said patient and an observer positioned on said axis outside said tunnel, said viewing system comprising a first mirror affixed to an interior wall of said tunnel substantially parallel to said axis, said first mirror being mounted substantially in front of and spaced from said patient when the latter is supported on said platform and a second mirror mounted to move with said platform, said second mirror being angularly adjustable to establish and visual path by way of said first and second mirror, said viewing system being disposed relative to said axially oriented patient to present said patient with an upright image of said observer.

2. Apparatus in accordance with claim 1 wherein said visual path between said patient and said observer includes a plurality of discrete linear path portions angularly disposed relative to each other, the path portion which terminates with said observer being substantially parallel to said axis.

3. Apparatus in accordance with claim 1 wherein said patient is supported in a substantially horizontal, supine position on said platform; and
said viewing system is located above said patient.

4. Apparatus in accordance with claim 1, wherein said tunnel includes forward and rear ends and an opening at said forward end adapted to admit said patient-bearing platform;
said patient being oriented in said tunnel with the patient's head pointed toward said rear tunnel end; and
said second mirror being adjustably mounted to enable said patient to sight outside said tunnel through said opening.

5. Apparatus in accordance with claim 4, wherein said platform includes a structure substantially surrounding the head of said patient and movable with said platform;
said second mirror being mounted on said structure; and
said structure including a window positioned to allow said patient to sight therethrough to said first mirror.

6. Apparatus in accordance with claim 5, wherein said first mirror extends substantially the full length of said tunnel.

7. Apparatus for visually communicating with a patient during the examination of the latter in a substantially linear diagnostic tunnel which surrounds at least a portion of said patient, said tunnel including forward and rear ends and an opening at said forward end;
said apparatus comprising;
a platform for supporting said patient in a supine, substantially horizontal position;
said platform being adapted to enter said tunnel through said opening with said patient positioned thereon parallel to the axis of said tunnel and oriented such that the patient's head points toward said rear tunnel end;
means for positioning said patient-bearing platform along said axis;
a helmet attached to said platform and substantially surrounding the head of said patient, said helmet including a window positioned to allow said patient to sight therethrough;
a viewing system mounted above said patient to permit a visual path to be established, at any axial position of said patient-bearing platform within said tunnel, between said patient and an observer positioned along said axis outside said tunnel;
said viewing system comprising a first mirror affixed to the interior roof of said tunnel parallel to said axis and extending substantially the full length of said tunnel, said first mirror being spaced from said patient when the latter is supported in said supine horizontal position on said platform; and
a second mirror mounted on said helmet, said second mirror being spaced from said patient and being positioned to be viewed by the latter through said window, said second mirror being angularly adjustable to establish said visual path through said window by way of said first and second mirrors and through said tunnel opening;
whereby said patient is presented with an upright image of said observer at any axial patient postiion within said tunnel.

* * * * *